United States Patent [19]

Bombardelli et al.

[11] Patent Number: 4,636,569
[45] Date of Patent: Jan. 13, 1987

[54] PHARMACEUTICAL COMPOSITIONS CONTAINING COMPOUNDS WITH A FLAVANONE SKELETON, PROCESS FOR THE PREPARATION OF THE SAID COMPOUND AND NOVEL COMPOUNDS OBTAINED

[75] Inventors: Ezio Bombardelli; Bruno Gabetta; Maria J. Magistretti, all of Milan, Italy

[73] Assignee: Inverni Della Beffa S.p.A., Milan, Italy

[21] Appl. No.: 587,684

[22] Filed: Mar. 6, 1984

[30] Foreign Application Priority Data

Mar. 10, 1983 [IT] Italy ................. 19993 A/83

[51] Int. Cl.⁴ ............................. C07D 311/04
[52] U.S. Cl. ...................................... 549/403
[58] Field of Search ........................... 549/403

[56] References Cited

U.S. PATENT DOCUMENTS

| | | | |
|---|---|---|---|
| 3,450,717 | 6/1969 | Krämer | 549/399 |
| 3,803,177 | 4/1974 | Jain | 549/403 |
| 3,816,466 | 6/1974 | Strandtmann et al. | 549/403 |

FOREIGN PATENT DOCUMENTS

| | | | |
|---|---|---|---|
| 0052086 | 5/1982 | European Pat. Off. | 549/403 |
| 0122053 | 10/1984 | European Pat. Off. | 549/403 |
| 0021678 | 2/1983 | Japan | 549/403 |

OTHER PUBLICATIONS

Chemical Abstracts 96:162388s (1982).

Merck Index, pp. 417–418, 9th edition, Merck & Co., Rahway, N.J. U.S.A. (1976).

Kishimoto, Y. "Pharmaceutical Studies on Ferns. XI. Flavonoids of Cyrtomium Species, (3), Constitution of Cyrtominetin and Cyrtopterinetin," *Chem. Pharm. Bull.*, vol. 4, pp. 24–26 (1956).

Kishimoto, Y. "Pharmaceutical Studies on the Ferns. IX. Flavonoids of Cyrtomium Species, 1, Flavonoid Aglycons", *Chem. Abstracts, 50:13894,* 1956.

Kirkiacharian et al., C. R. Acad. Sc., Paris, t. 280 (Mar. 17, 1975), p. 775.

*Primary Examiner*—Ethel G. Love
*Attorney, Agent, or Firm*—Browdy and Neimark

[57] ABSTRACT

Compounds with a flavanone skeleton having the formula I

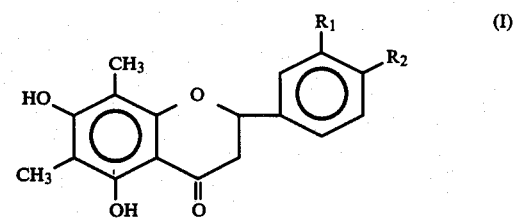

in which $R_1$ and $R_2$, which may be the same or different, represent hydrogen, hydroxyl, methoxyl, thiomethyl, amino or substituted amino, are endowed with expectorant, mucolytic, mucopoietic, choleretic and hypolipaemia-producing activity.

1 Claim, No Drawings

PHARMACEUTICAL COMPOSITIONS CONTAINING COMPOUNDS WITH A FLAVANONE SKELETON, PROCESS FOR THE PREPARATION OF THE SAID COMPOUND AND NOVEL COMPOUNDS OBTAINED

DESCRIPTION OF THE INVENTION

The present invention relates to novel pharmaceutical compositions containing flavanones as active ingredient and which are useful in the treatment of broncho-pulmonary and hepatic pathologies and pathologies of lipid metabolism. The invention also relates to methods of preparing the flavanones and to a class of the flavanones per se.

It is known that certain flavanones such as farrerol and eriodictyol (which are primarily of extractive origin and are present in small amounts in certain plants of the Ericaceae and Hydrophylaceae families), display expectorant and mucolytic activity. However the relatively low intensity of the pharmaceutical activity of these compounds, coupled with their low concentrations in natural sources has limited their practical applicability. Furthermore known methods for preparing flavanones (particularly 5,7-hydroxy-6,8-methyl substituted flavanones) suffer from the disadvantage that the necessary intermediates have only hitherto been prepared by routes which are not amenable to industrial application.

According to one aspect of the present invention there are provided novel pharmaceutical compositions useful in the treatment of broncho-pulmonary and hepatic pathologies and pathologies of the lipid metabolism containing, as active principle, compounds with a flavanone skeleton of general formula I

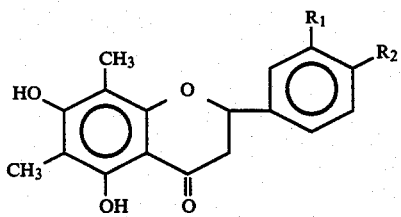

in which $R_1$ and $R_2$, which may be the same or different, represent hydrogen, hydroxyl, methoxyl, thiomethyl, or substituted or unsubstituted amino groups of the formula $-NR_3R_4$ wherein $R_3$ and $R_4$, which may be the same or different, represent hydrogen atoms or $C_{1-4}$ alkyl groups, or pharmaceutically acceptable acid addition or quaternary ammonium salts thereof.

The compounds of formula I in which both $R_1$ and $R_2$ represent methoxyl or at least one of them represents a thiomethyl, amino or substituted amino group are novel and form a further aspect of the invention. The compounds of formula I in which $R_1$ and $R_2$ represent hydrogen or hydroxyl, on the other hand, are known. However, no pharmacological or therapeutic activity of these known compounds has ever been described. As indicated above, while it is known that some flavanones, such as farrerol and eriodictyol, of predominantly extractive origin, have a limited expectorant and mucolytic activity, the compounds of formula I have unexpectedly been found to be endowed with a particularly intense expectorant, mucolytic and mucopoietic activities and also with significant choloretic and hypolipaemic-producing properties.

The present invention further provides a process for the preparation of compounds of formula I which is characterised by condensation of 2,4,6-trihydroxy-3,5-dimethylacetophenone with a substituted aromatic aldehyde of formula II in which $R_1$ and $R_2$ are as defined above in the presence of a base (see Scheme I below). Preferably the reaction is carried out in an alkaline medium. Although the nature of the reaction medium is not unduly critical, advantageously the medium comprises an organic solvent capable of forming an azeotropic mixture with water. The water evolved in the condensation may then be removed azeotropically. Thus for example the reaction may be carried out in a reaction medium comprising a mixture of piperidine and benzene or some other aromatic hydrocarbon.

As a further alternative the reaction may be carried out in an alcoholic solvent in the presence of an alkali metal hydroxide, although in this case, the phenolic hydroxyl groups should be protected, e.g. by esterification, in a manner known per se.

Scheme I

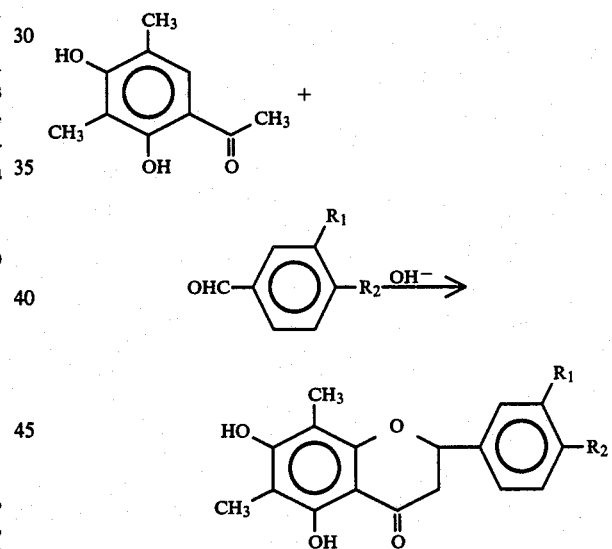

In an alternative procedure according to the invention 2,4,6-trihydroxy-1,3-dimethylbenzene may be reacted with acyl halides, particularly chlorides, of meta-para or para substituted cinnamic acids of formula II in which $R^1$ and $R^2$ are as defined above. (see Scheme II below)

Scheme II

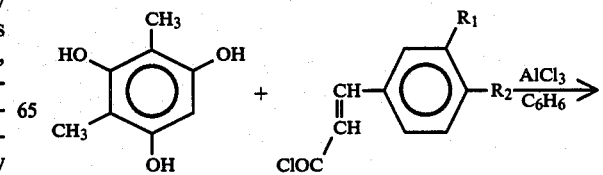

Scheme II -continued

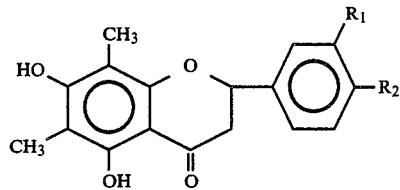

The dimethyl trihydroxyacetophenone and 2,4,6-trihydroxy-1,3-dimethyl benzene starting materials of these syntheses are substances which are known from the literature, but the reactions heretofore described for preparing them are not convenient to apply on an industrial scale and their yields are not satisfactory from a preparative point of view. The process of the invention provides novel methods for preparing these intermediates.

Thus dimethyl trihydroxyacetophenone, the base product for all the syntheses of the said flavanones, may be prepared according to the present invention in accordance with the following scheme (Scheme III):

Scheme III

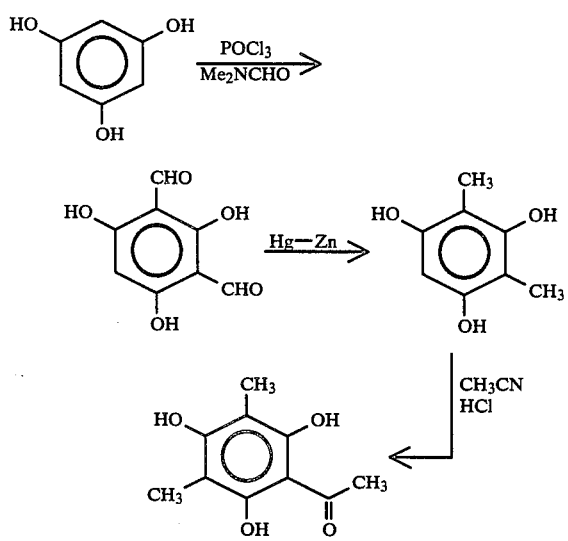

In this Scheme, phloroglucinol may be converted in almost quantitative yield to 2,4,6-trihydroxy-1,3-benzodialdehyde, by treatment with phosphorus oxychloride in dimethylformamide and subsequent acid hydrolysis. This intermediate may then be transformed into 2,4,6-trihydroxy-1,3-dimethylbenzene, by reduction of the -CHO function, for example by Clemmenson's method.

The 2,4,6-trihydroxy-1,3-dimethylbenzene may then be converted into 2,4,6-trihydroxy-3,5-dimethylacetophenone by condensation with acetonitrile in an acid medium in the presence of zinc chloride and with subsequent hydrolysis of the imine formed as intermediate.

Alternatively (Scheme IV) 2,4,6-trinitro-1,3-dimethyl-benzene may be reduced with iron in an acid medium to 2,4,6-triamino-1,3-dimethylbenzene, which in turn may be converted into 2,4,6-trihydroxy-1,3-dimethylbenzene by hydrolysis in the presence of acid.

Scheme IV

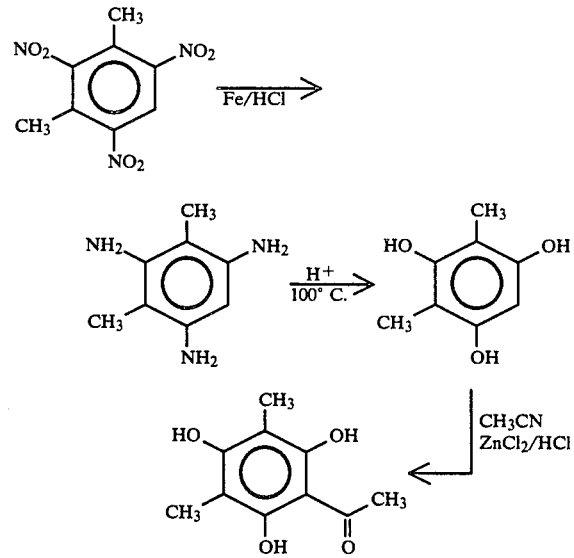

The subsequent transformation into trihydroxy-dimethylacetophenone may be effected by the method described above.

The synthesis of the final flavanones of formula I takes place, as described above, by condensation of the trihydroxydimethylacetophenone with an appropriate aromatic aldehydes in an alkaline medium. In particular the condensation may be carried out by operating in a mixture of piperidine and benzene or other suitable hydrocarbons such as toluene, xylene, etc., heated to reflux and from which the water which is generated in the condensation itself is continuously eliminated. Alternatively the reaction can be carried out in an alcoholic medium in the presence of hydroxides of sodium or potassium, utilizing in this case as starting materials not the phenolic compounds but their methyl esters.

In the case in which the methyl esters are employed as reaction intermediates, the methyl groups may be removed from the final product by heating the methylated flavanone in hydrobromic acid or by treating it with boron tribromide in chlorinated solvents, operating at temperatures between $-5°$ C. and $+40°$ C.

In order to purify the desired compounds, in the case where the condensation is effected in the presence of piperidine the reaction mixture may be diluted with solvents which are immiscible with water, such as ethyl acetate or methyl ethyl ketone, and extracted with dilute mineral acids such as hydrochloric, sulphuric, or phosphoric acid until complete elimination of the piperidine has been achieved.

The organic reaction phase may then be evaporated under vacuum and the residue is crystallized from solvents such as ethyl acetate, acetonitrile, acetone, pure alcohols or alcohols diluted with water.

If the reaction is effected in an alcoholic medium in the presence of hydroxides of sodium or potassium, the final product would generally be recovered by extraction with solvents which are immiscible with the reaction medium, diluted with water, acidified and, after evaporation of the organic phase, crystallized from suitable solvents.

If, a condensation involving the Friedel-Crafts reaction for obtaining the products of the present invention is used, in which trihydroxy-metaxylene is condensed with chlorides of substituted cinnamic acids in the presence of aluminium chlorides, the desired compounds may also be isolated by methods similar to those described above.

PHARMACEUTICAL DATA

The flavanones obtained by these syntheses are substances which are endowed with expectorant and mucolytic activities which are comparable with those of the best-known drugs used in this therapeutic field. However, they are further characterised by a lower toxicity and greater tolerability.

The said compounds are also useful as choleretics and as hypolipaemia-producing drugs and compared with known substances have an extremely high activity and in addition a perfect tolerability at effective doses.

EXPECTORANT ACTIVITY IN MICE

The expectorant activity of the compounds of the invention was evaluated by the method of Nawatarih (Kagoshima Daigaku Igaku Zasshi 27, 561, 1976) with fluorescein, according to which the increment of colouring matter excreted in the bronchial liquid is determined experimentally in mice. In the experiments the activity of 6,8-dimethyl-5,7,3',4'-tetrahydroxyflavanone was evaluated in comparison with that of bromhexine hydrochloride as reference standard. The results, given in Table 1, are expressed in $ED_{50}$ (dose capable of incrementing the excretion of the colouring matter by 50%).

TABLE 1

| Expectorant activity (according to Nawatarih) | | |
|---|---|---|
| Compound | Administration route | $ED_{50}$ (mg/kg) |
| 6,8-Dimethyl-5,7,3',4'-tetrahydroxyflavanone | Oral | 78 |
| Bromhexine HCl | Oral | 51 |

From the values given above and from the acute toxicity ($LD_{50}$) data after oral administration to mice given below, it is apparent that 5,8-dimethyl-5,7,3',4'-tetrahydroxyflavanone is endowed with a therapeutic index which is distinctly more favourable than that of bromhexine.

The expectorant activity has also been monitored by the Perry and Boyd method (J. Pharmacol. Exp. Ther. 7 580, 1941), in which the direct amount of expectoration is determined in the rabbit. 6,8-Dimethyl-5,7,3',4'-tetrahydroxyflavanone has been shown to have an $ED_{50}$ of 200 mg/kg/os.

ACUTE TOXICITY ($LD_{50}$ in mice (oral route)

| | |
|---|---|
| 6,8-Dimethyl-5,7,3',4'-tetrahydroxy-flavanone | *$LD_0$ = 3000 mg/kg |
| Bromhexine HCl | $LD_{50}$ = 2135 mg/kg |

*(No deaths occurred at a dose rate of 3000 mg/kg)

CHOLERETIC ACTIVITY IN RATS

The choleretic activity, compared to that of catechol, has been determined in rats by measuring both the bile flow and the excretion of cholate (cholic acid).

Administration of 6,8-dimethyl-5,7,4'-trihydroxyflavanone resulted in the data given in Table 2.

TABLE 2

| | | choleretic activity | | |
|---|---|---|---|---|
| | Dose | Number of animals | Bile flow ml/4 h | Total cholate mg/4 h |
| Controls | — | 10 | 2.72 ± 0.11 | 11.64 ± 0.19 |
| 6,8-Dimethyl-5,7,4'-tri-hydroxy-flavanone | 200 | 10 | 5.25 ± 0.18*** | 15.23 ± 0.97** |
| (+)Catechol | 200 | 10 | 4.13 ± 0.4** | 13.03 ± 0.35** |

**The average obtained between the two groups is significantly different ($P < 0.01$) according to Student's t-test.
***The average obtained between the two groups is significantly different ($P < 0.001$) according to Student's t-test.

HYPOLIPAEMIC ACTIVITY IN RATS

The hypolipaemia-producing activity was evaluated in other tests in which the variations in cholesterol, triglycerides, NEFA (non-esterified fatty acids) and various lipoprotein fractions were determined.

In Table 3 there is reported the effect of 6,8-dimethyl-5,7,4'-trihydroxyflavanone and of nicotinic acid in combatting olive oil induced hyperlipaemia in rats fasted for 16 hours. The substances under test were administered orally two hours before the lipid load and the hyperlipaemia was induced by administering orally 20 ml/kg of olive oil.

Sacrifice took place three hours after the administration of the oil.

TABLE 3

| | Hypolipaemic activity | | | |
|---|---|---|---|---|
| | Dose mg/kg os | Number of animals | NEFA uEq/l m ± ES | Triglycerides mg/100 ml m − ES |
| Controls - NaCl 0.9% | — | 6 | 1017 ± 39 | 252 ± 18 |
| 6,8-dimethyl-5,7,4'-trihydroxy-flavanone | 50 | 6 | 702 ± 23 (−31) | 198 ± 7 (−61) |
| Nicotinic acid | 173 | 6 | 709 ± 33 (−30) | 71 ± 6 (−72) |

CONCLUSIONS

For all the activities examined, the products show a linearity of response between dose and effect. Even high doses administered repeatedly do not cause organic or somatic side-effects worth mentioning.

The theraupeutic dose to be used for humans in the clinical range is about 100–1000 mg/day taken or given orally or rectally and administerable in solid or liquid pharmaceutical forms, e.g. capsules, tablets sugar-coated pills, syrups, suppositories, etc.

EXAMPLES

The following Examples further illustrate the invention.

PREPARATION 1

(a) Synthesis of 2,4,6-triamino-1,3-dimethylbenzene sulphate 560 grams (2.32 mols) of 1,3-dimethyl-2,4,6-trinitrobenzene are suspended in 1.5 liter of aqueous ethanol and 1.070 kg (19.1 mols) of iron in powder form are added while stirring. The reaction mixture is heated to boiling and while still stirring 0.06 liters of concentrated hydrochloric acid are added over a period of about 3 hours. The heating is maintained for another three hours and then the suspension is filtered to elminate iron oxide and polymerized by-products.

After cooling to 20° C., the filtrate is treated with 0.7 kg of concentrated sulphuric acid. After the acid solution has remained in a refrigerator over night, 0.65 kg of 2,4,6-triamino-1,3-dimethylbenzene sulphate having a degree of purity of 90% crystalline. This is usable for the following operations of the synthesis.

(b) Synthesis of 2,4,6-trihydroxy-1,3-dimethylbenzene 0.65 kg of 2,4,6-triamino-1,3-dimethylbenzene sulphate is dissolved in 6.5 liters of a 0.2N buffer solution of potassium chloride/hydrochloric acid. The reaction mixture is heated to weak reflux for 48 hours in a nitrogen atmosphere and when the reaction is complete, the whole is cooled and extracted three times using 3 liters of ethyl acetate each time. The organic phase is dehydrated over anhydrous sodium sulphate and then evaporated under vacuum at a temperature of 50° C. to about 0.6 liters. By crystallization from benzene, this concentrate supplies 0.21 kg of 2,4,6-trihydroxy-1,3-dimethylbenzene having the following chemicophysical characteristics:

| Melting Point | 160° C. |
|---|---|
| Mass of molecular ion (M+) | m/z = 154 |
| Elemental analysis | C 61.9; H 6.8 |
| ($C_8H_{10}O_3$ requires C 62.3; H 6.5) | |

PREPARATION 2

(a) Synthesis of 2,4,6-trihydroxy-1,3-dimethylbenzene 0.6 kg of phloroglucinol is dissolved in 1.4 liters of dioxan and a mixture containing 0.8 liters of N,N-dimethylformamide and 0.96 liters of phosphorus oxychloride is added slowly and with vigorous stirring. The addition of the reagent having been completed, the reaction is maintained at 40° C. for 12 hours containing the stirring and then the whole is poured over 10 kg of crushed ice.

The solution obtained is left to stand for 24 hours so as to permit the crystallization of 2,4,6-trihydroxy-1,3-benzene-dialdehyde. The crystalline mass is filtered and recrystallized from ethyl acetate to obtain 0.61 kg of product having the following chemicophysical characteristics:

| Mass of molecular ion (M+) | m/z = 182 |
|---|---|
| Elemental analysis | C 51.3; H 3.5 |
| ($C_8H_6O_5$ requires C 52.8; H 3.3) | |

(b) 0.61 kg of 2,4,6-trihydroxybenzenedialdehyde is placed in a vessel equipped with a stirrer and a dropping device and zinc amalgam, obtained by normal procedures from 3 kg of Zn and 0.6 kg of $HgCl_2$, is added. 1.5 liters of concentrated hydrochloric acid are added to the suspension with vigorous stirring and slowly. The reaction temperature is 80° C. After two hours, the reaction mass is cooled and filtered. The aqueous solution containing the product is extracted three times with 1 liter of ethyl acetate. The combined organic extracts are concentrated to dryness under vacuum. The residue weighs 0.52 kg and is dissolved in 0.450 liters of acetonitrile and 3.5 liters of ethyl ether. When dissolution is complete, 0.5 kg of hydrochloric acid is added over a period of about three hours and the whole is left to stand for 48 hours.

An abundant precipitate forms which is separated by decanting and after dilution with 4 liters of water is heated at 100° C. for 5 hours.

After cooling of the solution and filtration, 0.46 kg of crude 2,4,6-trihydroxy-3,5-dimethylacetophenone are obtained, which is recrystallized from ethyl acetate to yield 0.42 kg of pure 2,4,6-trihydroxy-3,5-dimethylacetophenone.

EXAMPLE 1

6,8-dimethyl-5,7,3',4'-tetrahydroxyflavanone (cyrtominetin)

(a) Synthesis of 2,4,6-trihydroxy-3,5-dimethylacetophenone 0.21 kg of 2,4,6-trihydroxy-1,3-dimethylbenzene prepared in accordance with Preparation 1 or 2 is dissolved in 10 volumes of a mixture constituted by 2 parts of acetonitrile and 8 parts of ethyl ether. To this solution there are added 0.09 kg of zinc chloride and 0.2 kg of gaseous hydrochloric acid, the temperature being maintained at a value between 0° C. and 10° C. The reaction mixture is then left to stand for three days at room temperature. The solid formed is separated by decantation and, still moist with solvent, is suspended in 2.5 liters of water and is then heated to reflux for 5 hours, checking that the internal temperature is higher than 90° C. By cooling the solution followed by filtration, 0.19 kg of 2,4,6-trihydroxy-3,5-dimethylacetophenone are obtained.

The product obtained is crystallized from ethyl acetate, yielding 0.175 kg of pure 2,4,6-trihydroxy-3,5-dimethylacetophenone having the following chemicophysical characteristics:

| Melting Point | 218° C. |
|---|---|
| Mass of molecular ion (M+) | m/z = 196 |
| Elemental analysis | C 60.9; H 6.1 |
| ($C_{10}H_{12}O_4$ requires C 61.2; H 6.2) | |

(b) Synthesis of 6,8-dimethyl-5,7,3',4'-tetrahydroxyflavanone 0.13 kg of 2,4,6-trihydroxy-3,5-dimethylacetophenone are dissolved in 1.3 liters of a 1:1 mixture of piperidine and benzene. This mixture is heated to weak reflux and 0.082 kg of 3,4-dihydroxybenzaldehyde is added in small portions, the whole being then kept boiling for 24 hours. The reaction is effected in an apparatus which allows the elimination of the water which is formed during the condensation. When condensation is complete, the benzene is eliminated by distillation under vacuum and the reaction mixture is poured into 4 liters of an aqueous solution of hydrochloric acid cooled to 0° C. The acid aqueous phase (pH 3.5) is then extracte three times with 1 liter of ethyl acetate and the combined organic phrases are dehydrated over anhydrous sodium sulphate and concentration under vacuum to 0.5 liters.

0.12 kg of practically pure 6,8-dimethyl-5,7,3',4'-tetrahydroxyflavanone having the following chemicophysical and spectroscopic characteristics are obtained by crystallization:

| Melting Point | 225-228° C. |
|---|---|
| Mass of molecular ion (M+) | m/z = 316 |

-continued

| UV $E_{1\,cm}^{1\%}$ at 292 nm | 552.6 |
| --- | --- |
| Elemental analysis | C 64.1; H 5.4 |
| ($C_{17}H_{16}O_6$ requires C 64.5; H 5.1) | |

EXAMPLE 2

6,8-Dimethyl-5,7-dihydroxy-4'-thiomethylflavanone 0.13 Kg of 2,4,6-trihydroxy-3,5-dimethylacetophenone, prepared as in Example 1(a), is mixed with 0.09 kg of 4-methylmercaptobenzaldehyde and dissolved in 0.6 liters of a 1:2 mixture of piperidine and benzene and the whole is heated to weak reflux for 5 hours in an apparatus which allows elimination of the water.

When condensation is complete, the benzene is eliminated under vacuum and the residue is poured into 2 liters of dilute hydrochloric acid. The acid aqueous phase is then extracted three times with 0.5 liters of ethyl acetate.

The combined organic phases, after dehydration over sodium sulphate, are concentrated to dryness under vacuum and the residue is crystallized from 2 parts by volume of acetonitrile.

After filtration and drying, there is obtained 0.1 kg of 6,8-dimethyl-5,7-dihydroxy-4'-thiomethylflavanone having the following chemicophysical and spectroscopic characteristics:

| Melting Point | 170–172° C. |
| --- | --- |
| Mass of molecular ion (M+) | m/z = 346 |
| UV $E_{1\,cm}^{1\%}$ | |
| at 260 nm | |
| at 297 nm | 565 |
| Elemental analysis | C 65.4; H 5.7 |
| ($C_{18}H_{18}SO_5$ requires C 65.4; H 5.5) | |

EXAMPLE 3

Synthesis of 6,8-dimethyl-5,7,4'-trihydroxy-3'-methoxyflavanone 0.1 kg of 2,4,6-trihydroxy-3,5-dimethylacetophenone prepared as in Example 1(a) is mixed with 0.073 kg of vanillin and the whole is dissolved in 2 liter of a 1:1 mixture of benzene and piperidine and heated to weak reflux for 24 hours. When condensation is complete, the solution is diluted with 2 liters of ethyl acetate and washed with aqueous hydrochloric acid until the piperidine is eliminated.

0.95 kg of 6,8-dimethyl-5,7,4'-trihydroxy-3'-methoxyflavanone having the following characteristics are obtained by concentration of the organic phase and crystallization of the residue from acetone.

| Melting Point | 146–148° C. |
| --- | --- |
| Mass of molecular ion (M+) | m/z = 330 |
| $E_{1\,cm}^{1\%}$ at 294 nm | 526 |
| Elemental analysis | C 64.6; H 5.7 |
| ($C_{18}H_{18}O_6$ requires C 65.4; H 5.5) | |

EXAMPLE 4

Synthesis of 6,8-dimethyl-5,7-dihydroxy-4'-(dimethylamino)-flavanone 0.1 Kg of 2,4,6-trihydroxy-3,5-dimethylacetophenone prepared as in Example 1(a) is mixed with 0.071 kg of p-dimethylaminobenzaldehyde and the whole is dissolved in 2 liters of a 1:2 mixture of piperidine and benzol and heated to weak reflux for 8 hours in an apparatus which allows elimination of the water. When condensation is complete, the reaction mixture is cooled and is left at room temperature for 12 hours. 0.85 kg of product crystallizes and is recrystallized from 1.2 liters of methyl ethyl ketone.

After filtration and drying, there is obtained 0.8 kg of 6,8-dimethyl-5,7-dihydroxy-4'-(dimethylamino)-flavanone having the following chemicophysical and spectroscopic characteristics:

| Melting Point | 212–215° C. |
| --- | --- |
| Mass of molecular ion (M+) | m/z = 327 |
| $E_{1\,cm}^{1\%}$ | |
| at 261 nm | |
| at 296 nm | 664 |
| Elemental analysis | C 68.9; H 6.6 N 4.3 |
| ($C_{19}H_{21}NO_4$ requires C 69.7; H 6.5 N 4.3) | |

PHARMACEUTICAL EXAMPLES

EXAMPLE 5

A syrup containing 6,8-methyl-5,7,3',4'-tetrahydroxyflavanone as active principle was prepared from the following ingredients.

| 6,8-dimethyl-5,7,3',4'-tetrahydroxyflavanone | 1 g |
| --- | --- |
| Polyoxyethylenated hydrogenated castor oil (40-OE) or polysorbates | 15 g |
| Sucrose | 40 g |
| Propylene glycol | 5 g |
| Ethyl alcohol | 10 g |
| Mixture of p-hydroxybenzoates | 0.1 g |
| Aromatizing agent | 0.5–1 g |
| Purified water q.s.f. | 100 ml |

EXAMPLE 6

Capsules containing 6,8-dimethyl-5,7,3',4'-tetrahydroxyflavanone were prepared by admixing in bulk the ingredients listed below in proportions such that each 220 mg capsule contains:

| 6,8-Dimethyl-5,7,3',4'-tetrahydroxyflavanone | 150 mg |
| --- | --- |
| Lactose | 64 mg |
| PVP (polyvinyl pyrrolidone) 30,000 Mol. wt. | 3 mg |
| Magnesium stearate | 3 mg |

EXAMPLE 7

Suppositories containing 6,8-dimethyl-5,7,3',4'-tetrahydroxyflavanone were prepared by admixing and melting a bulk formulation of the ingredients listed below and moulding the suppositories. Each 1.5 g suppository contains:

| 6,8-dimethyl-5,7,3',4'-tetrahydroxyflavanone | 150 mg |
| --- | --- |
| Polyoxyethyl sorbitan monostearate | 125 mg |
| Mono-di- and triglycerides of vegetable fatty acids | 1125 mg |

EXAMPLE 8

Suppositories for children containing 6-8-dimethyl-5,7,3',4'-tetrahydroxyflavanone were prepared as in Example 7 to the following formulation. Each 1 g suppository contains:

| | |
|---|---|
| 6,8-dimethyl-5,7,3',4'-tetrahydroxyflavanone | 75 mg |
| Polyoxyethylene sorbitan monostearate | 75 mg |
| Mono-di-triglycerides of vegetable fatty acids | 850 mg |

We claim:
1. A method of treatment of a patient in need of a mucoregulating agent, comprising administering to such patient a mucoregulating amount of 6,8-dimethyl-5,7,3',4'-tetrahydroxyflavanone.

* * * * *